United States Patent
Nakajima

(10) Patent No.: US 10,653,322 B2
(45) Date of Patent: May 19, 2020

(54) PHOTOACOUSTIC APPARATUS, METHOD OF ACQUIRING SUBJECT INFORMATION, AND NON-TRANSITORY COMPUTER READABLE MEDIUM

(71) Applicant: CANON KABUSHIKI KAISHA, Tokyo (JP)

(72) Inventor: Takao Nakajima, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 861 days.

(21) Appl. No.: 15/305,613

(22) PCT Filed: Apr. 20, 2015

(86) PCT No.: PCT/JP2015/002141
§ 371 (c)(1),
(2) Date: Oct. 20, 2016

(87) PCT Pub. No.: WO2015/162899
PCT Pub. Date: Oct. 29, 2015

(65) Prior Publication Data
US 2017/0042429 A1 Feb. 16, 2017

(30) Foreign Application Priority Data
Apr. 23, 2014 (JP) ................. 2014-089307

(51) Int. Cl.
*A61B 5/145* (2006.01)
*A61B 5/00* (2006.01)

(52) U.S. Cl.
CPC ........ *A61B 5/0095* (2013.01); *A61B 5/14542* (2013.01); *A61B 5/743* (2013.01); *A61B 2560/0223* (2013.01)

(58) Field of Classification Search
CPC .... A61B 5/0095; A61B 5/14542; A61B 5/743
See application file for complete search history.

(56) References Cited

U.S. PATENT DOCUMENTS 5,348,002 A * 9/1994 Caro ............... A61B 5/0095
600/310
5,713,356 A 2/1998 Kruger
(Continued)

FOREIGN PATENT DOCUMENTS

| JP | 2010-88627 A | 4/2010 |
|---|---|---|
| WO | 2011/052061 A1 | 3/2013 |
| WO | 2013/188707 A1 | 12/2013 |

OTHER PUBLICATIONS

Xia, J., et al., "Calibration-free quantification of absolute oxygen saturation based on the dynamics of photoacoustic signals", Optics Letters, Aug. 1, 2013, pp. 2800-2803, vol. 38, No. 15.
(Continued)

*Primary Examiner* — Eric F Winakur
(74) *Attorney, Agent, or Firm* — Canon U.S.A., Inc., IP Division

(57) ABSTRACT

A photoacoustic apparatus includes a light source configured to generate a plurality of light beams having wavelengths different from each other, a conversion element configured to receive a photoacoustic wave that is generated in a subject in response to being illuminated with the respective light beams having wavelengths different from each other and output a signal for each wavelength, an information acquisition unit configured to acquire information in terms of a concentration of a substance existing in the subject by using the signal for each wavelength, and a specifying unit configured to specify a coefficient and instruct the information acquisition unit to use the specified coefficient in acquiring the information in terms of the concentration, wherein the specifying unit specifies, as the coefficient, a value representable by a formula including an amount of light having each wavelength, and wherein the information acquisition unit acquires information in terms of the concentration by (Continued)

using the coefficient specified by the specifying unit and the signal for each wavelength.

18 Claims, 6 Drawing Sheets

(56) References Cited

U.S. PATENT DOCUMENTS

| | | | |
|---|---|---|---|
| 6,498,942 B1 * | 12/2002 | Esenaliev | A61B 5/0095 600/310 |
| 2006/0264717 A1 | 11/2006 | Pesach et al. | |
| 2013/0245406 A1 | 9/2013 | Wang et al. | |
| 2013/0245418 A1 | 9/2013 | Oishi | |
| 2013/0281842 A1 | 10/2013 | Lorenzo et al. | |
| 2014/0049770 A1 | 2/2014 | Li et al. | |

OTHER PUBLICATIONS

Zhang, H.F., et al, "Imaging of hemoglobin oxygen saturation variations in single vessels in vivo using photoacoustic microscopy", Applied Physics Letters, 2007, pp. 053901-1-pp. 053901-3, vol. 90.

* cited by examiner

[Fig. 1]
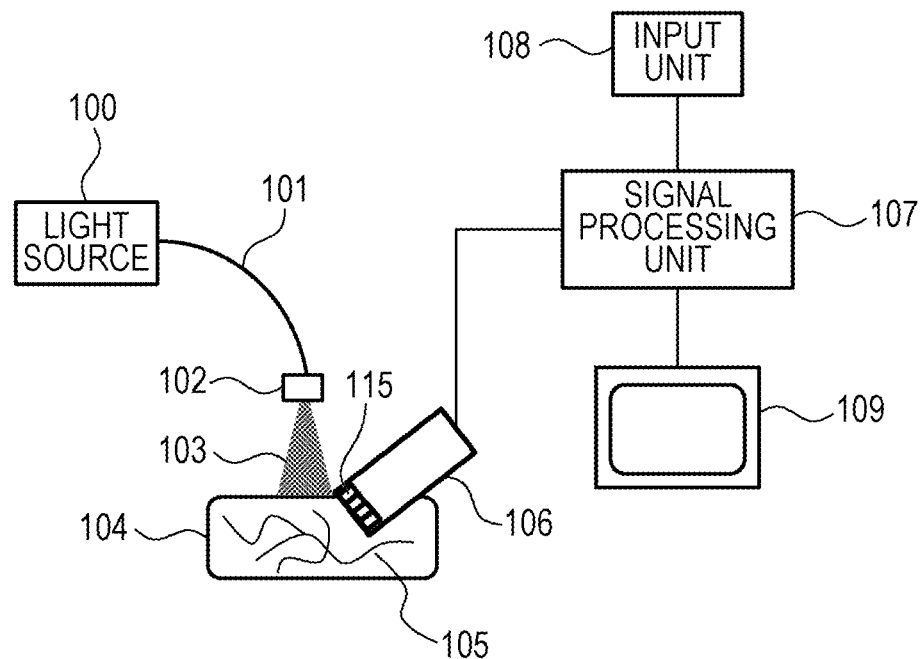

[Fig. 2A]
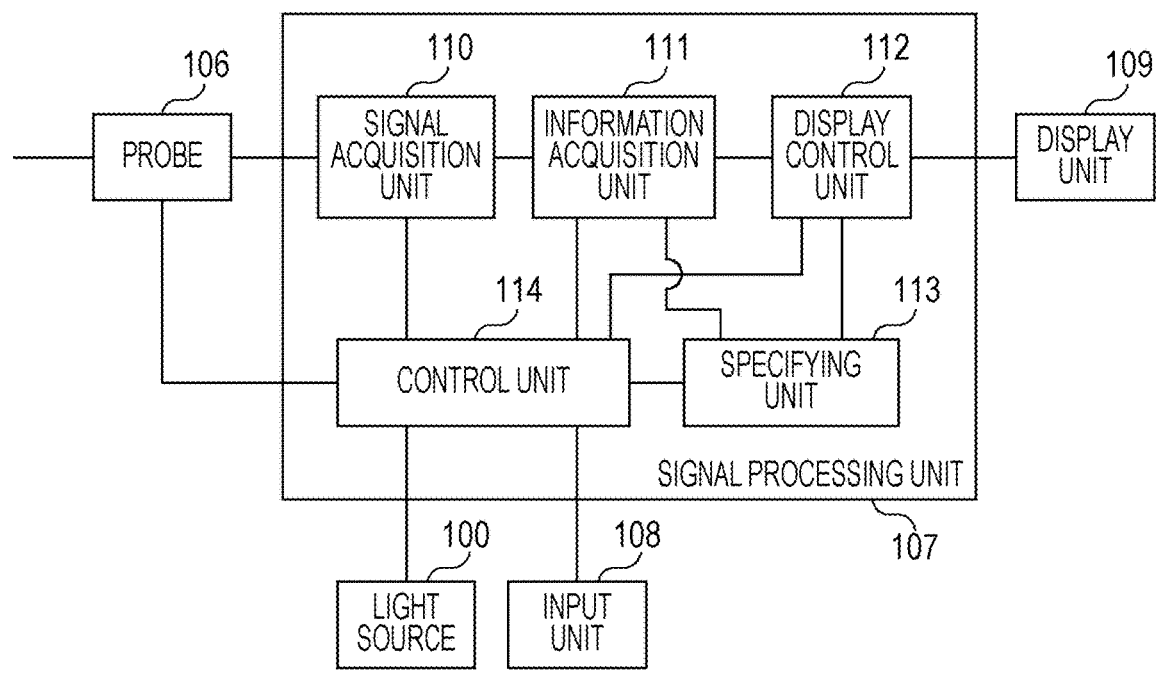
[Fig. 2B]
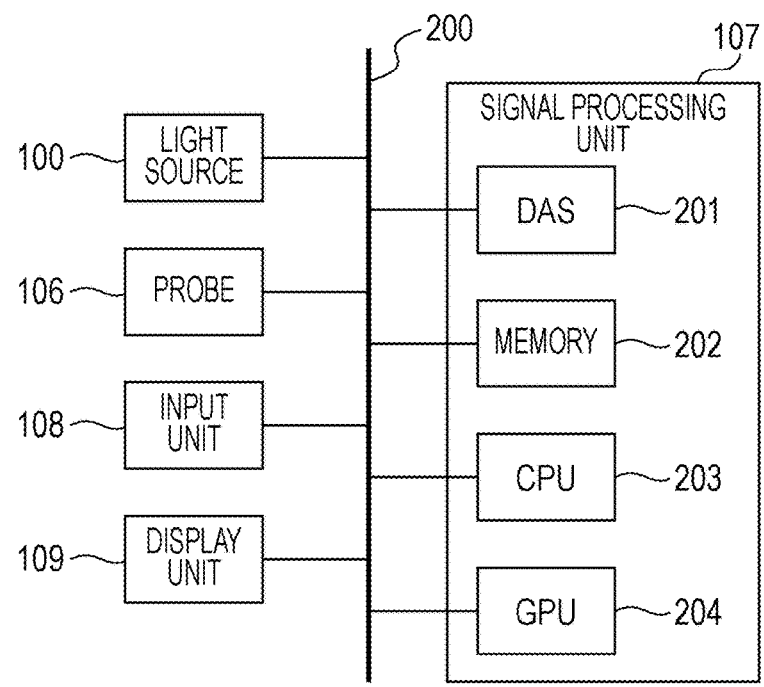

[Fig. 3]
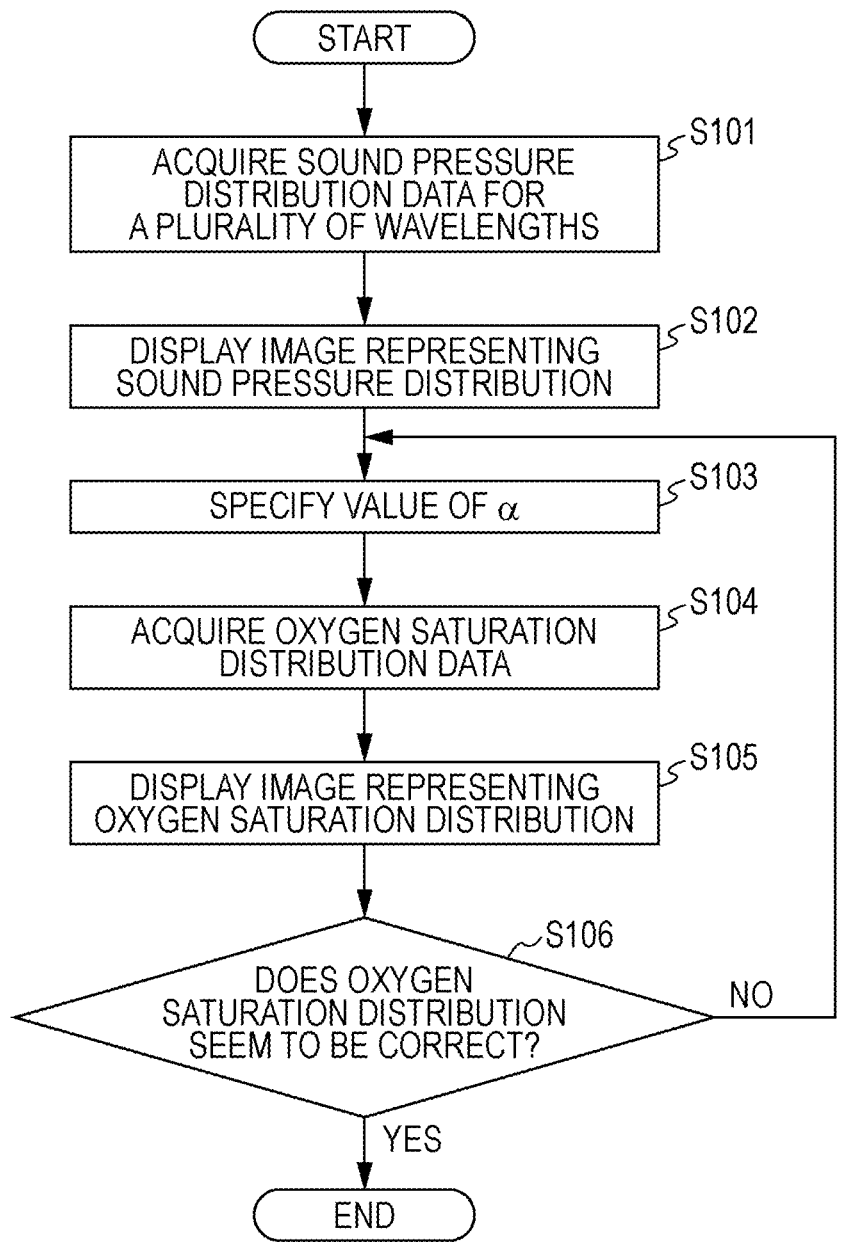

[Fig. 4]
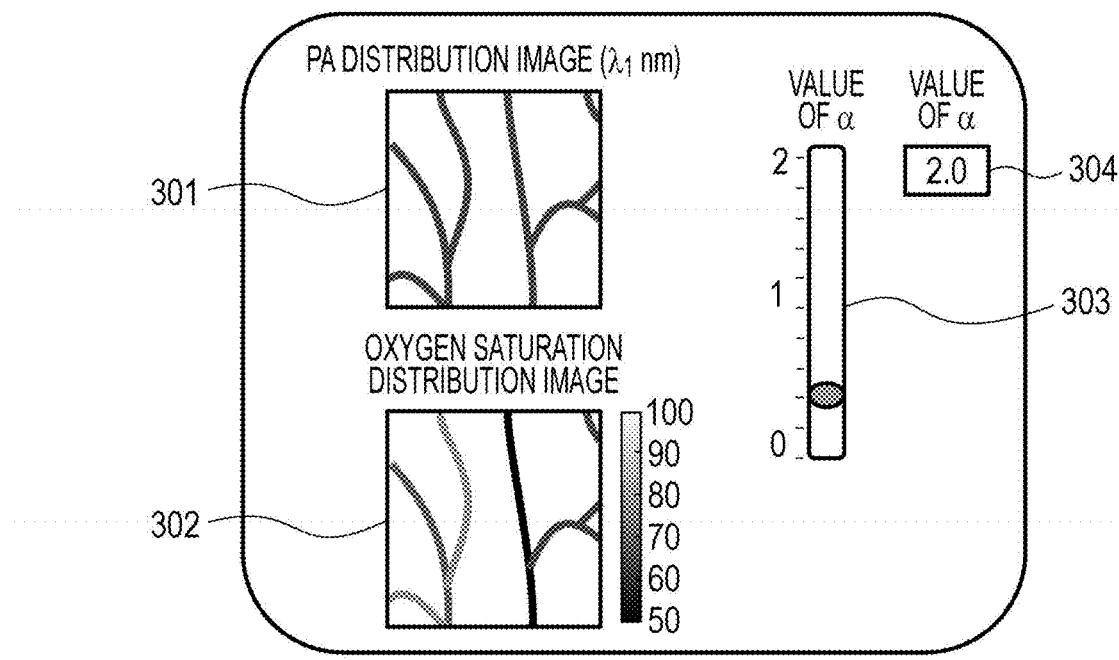

[Fig. 5]
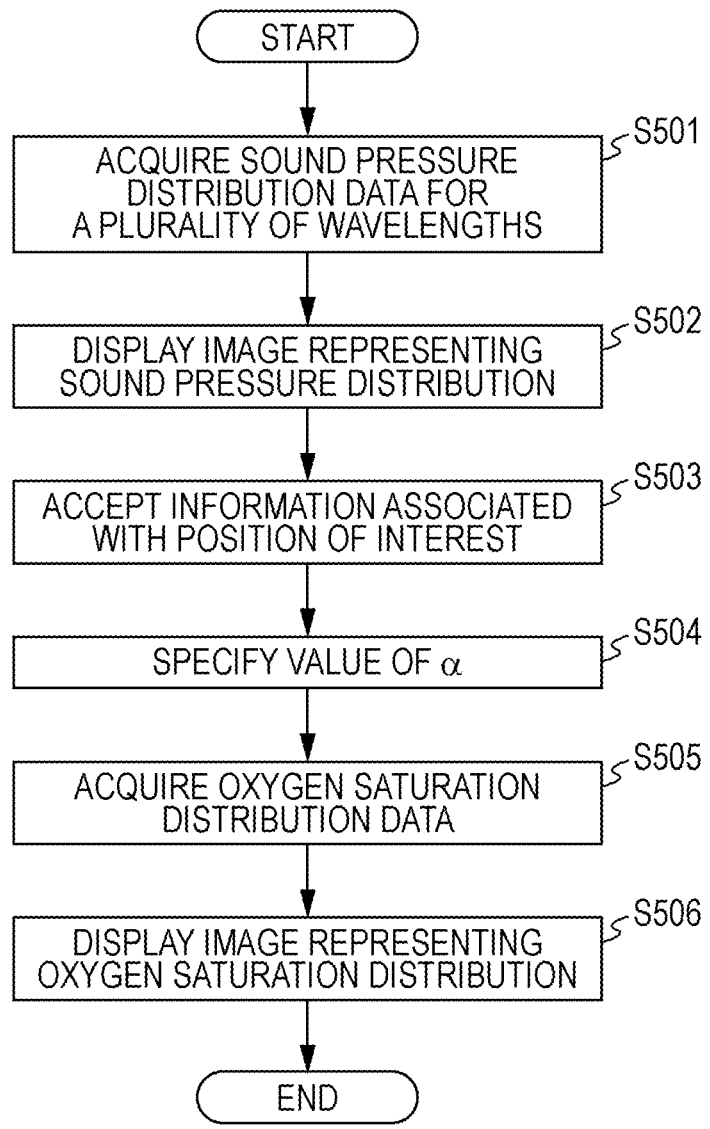

[Fig. 6]
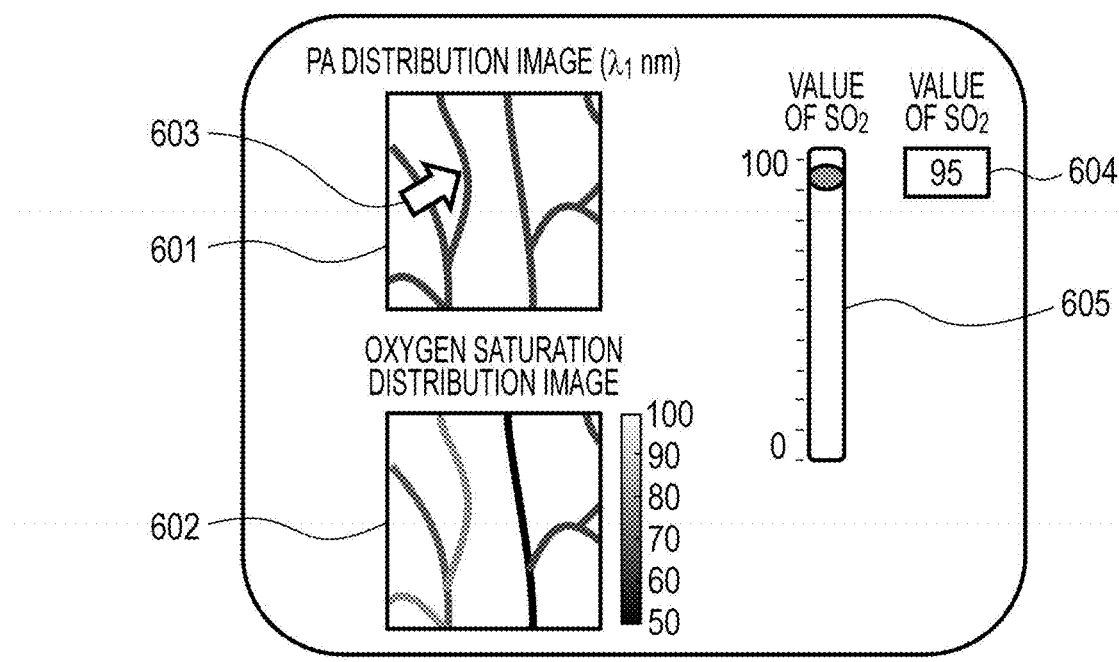

PHOTOACOUSTIC APPARATUS, METHOD OF ACQUIRING SUBJECT INFORMATION, AND NON-TRANSITORY COMPUTER READABLE MEDIUM

TECHNICAL FIELD

The present invention relates to a photoacoustic apparatus, a method of acquiring subject information, and a non-transitory computer readable medium, and more particularly, to a technique using a photoacoustic wave that is generated when light ray is absorbed.

BACKGROUND ART

A photoacoustic imaging technique is known as one of imaging techniques using light. In the photo acoustic imaging, first, pulsed light is generated by a light source and a subject is illuminated with the pulsed light. In the subject, the illumination light propagates while diffusing. Energy of light is absorbed by a plurality of parts in the subject, which may cause acoustic waves to be generated (hereafter, such an acoustic wave will be referred to as a photoacoustic wave). The photoacoustic waves are received by a transducer, and received signals are analyzed by a processing apparatus. As a result, information in terms of optical characteristic values of internal portions of the subject is obtained, and an optical characteristic value distribution in the inside of the subject is visualized.

By illuminating the subject with light having different wavelengths, it is possible to obtain a distribution of a concentration of a substance existing in the subject. In this case, more specifically, an optical coefficient (absorption coefficient μa) of an internal portion of the subject is determined for each wavelength, and then a distribution of a concentration of a substance is determined and visualized based on the substance-specific dependence of the optical coefficient on the wavelength. In particular, based on the concentration of oxyhemoglobin HbO and the concentration of deoxyhemoglobin Hb, it is possible to acquire the oxygen saturation in blood. In a case where two wavelengths are used, the oxygen saturation $SO_2$ may be determined according to formula (1) described below.

[Math. 1]

$$SO_2(r) = \frac{[HbO_2]}{[HbO_2] + [Hb]} \quad (1)$$

$$= \frac{\frac{\mu_a^{\lambda_2}(r)}{\mu_a^{\lambda_1}(r)} \cdot \varepsilon_{Hb}^{\lambda_1} - \varepsilon_{Hb}^{\lambda_2}}{\left(\varepsilon_{HbO}^{\lambda_2} - \varepsilon_{Hb}^{\lambda_2}\right) - \frac{\mu_a^{\lambda_2}(r)}{\mu_a^{\lambda_1}(r)} \cdot \left(\varepsilon_{HbO}^{\lambda_1} - \varepsilon_{Hb}^{\lambda_1}\right)}$$

In formula (1), $\mu_a^{\lambda_1}$ denotes an absorption coefficient at a wavelength $\lambda_1$, and $\mu_a^{\lambda_2}$ denotes an absorption coefficient at a wavelength $\lambda_2$. Furthermore, $\varepsilon_{Hbo}^{\lambda_1}$ denotes a molecular extinction coefficient of oxyhemoglobin at the wavelength $\lambda_1$, and $\varepsilon_{Hb}^{\lambda_1}$ denotes a molecular extinction coefficient of deoxyhemoglobin at the wavelength $\lambda_1$. $\varepsilon_{Hbo}^{\lambda_2}$ denotes a molecular extinction coefficient of oxyhemoglobin at the wavelength $\lambda_2$, and $\varepsilon_{Hb}^{\lambda_2}$ denotes a molecular extinction coefficient of deoxyhemoglobin at the wavelength $\lambda_2$. Note that values of $\varepsilon_{Hbo}^{\lambda_1}$, $\varepsilon_{Hb}^{\lambda_1}$, $\varepsilon_{Hbo}^{\lambda_2}$, and $\varepsilon_{Hb}^{\lambda_2}$ are known. Furthermore, r denotes a position coordinate. To determine the oxygen saturation in blood, as may be seen from formula (1), it is necessary to determine the ratio of the absorption coefficient between two wavelengths.

On the other hand, an initial sound pressure $P_0$ of a photoacoustic wave generated by an absorber in the subject as a result of light absorption is given by a following formula.

[Math. 2]

$$P_0 = \Gamma \cdot \mu_a \cdot \Phi \quad (2)$$

where $\Gamma$ denotes a Gruneisen coefficient which is given by a coefficient of volume expansion (β) times a sound speed (c) squared divided by a specific heat at constant pressure ($C_p$). $\Phi$ denotes an amount of light at a particular position (in a local region), which is an amount of light falling on an absorber and is also called a light fluence. It is possible to calculate the initial sound pressure ($P_0$) using a reception signal (PA signal) output from a probe that receives the photoacoustic wave.

From formula (2), the value of the ratio of the absorption coefficient between two wavelengths is given as follows.

[Math. 3]

$$\frac{\mu_a^{\lambda_2}(r)}{\mu_a^{\lambda_1}(r)} = \frac{\Phi^{\lambda_1} \cdot P_0^{\lambda_2}}{\Phi^{\lambda_2} \cdot P_0^{\lambda_1}} \quad (3)$$

To determine the value of the ratio of the absorption coefficient, as may be seen from formula (3), it is necessary to determine the amount of light $\Phi^{\lambda_1}$ at the wavelength $\lambda_1$ and the amount of light $\Phi^{\lambda_2}$ at the wavelength $\lambda_2$. In the apparatus disclosed in PTL 1, light emitted from the inside of a subject is measured using a photodiode, and an average optical coefficient of the subject is determined from the measured light, and then a distribution of an amount of light $\Phi$ in the inside of the subject is calculated from the optical coefficient.

In the case of a method such as that disclosed in PTL 1, to estimate the distribution of the amount of light $\Phi$ in the inside of a subject, a procedure of determining an optical coefficient of a subject is necessary, which needs complicated processing and/or complicated system configuration. In view of the above, the present invention provides a simpler method of acquiring information in terms of a concentration.

CITATION LIST

Patent Literature

PTL 1: Japanese Patent Laid-Open No. 2010-88627
PTL 2: U.S. Pat. No. 5,713,356

SUMMARY OF INVENTION

According to an aspect of the invention, a photoacoustic apparatus includes a light source configured to generate a plurality of light beams having wavelengths different from each other, a conversion element configured to receive a photoacoustic wave that is generated in a subject in response to being illuminated with the respective light beams having wavelengths different from each other and output a signal for each wavelength, an information acquisition unit configured to acquire information in terms of a concentration of a substance existing in the subject by using the signal for each wavelength, and a specifying unit configured to specify a coefficient and instruct the information acquisition unit to use the specified coefficient in acquiring the information in terms of the concentration, wherein the specifying unit specifies, as the coefficient, a value representable by a formula including an amount of light having each wavelength, and wherein the information acquisition unit acquires information in terms of the concentration by using the coefficient specified by the specifying unit and the signal for each wavelength.

Further features of the present invention will become apparent from the following description of exemplary embodiments with reference to the attached drawings.

BRIEF DESCRIPTION OF DRAWINGS

FIG. 1 is a schematic diagram illustrating an overall configuration of a photoacoustic apparatus according to a first embodiment.

FIG. 2A is a block diagram illustrating a configuration of a signal processing unit according to the first embodiment.

FIG. 2B is a block diagram illustrating connections to external units.

FIG. 3 is a flow chart illustrating an example of a processing flow according to the first embodiment.

FIG. 4 is a diagram illustrating an example of a display screen according to the first embodiment.

FIG. 5 is a flow chart illustrating an example of a processing flow according to a second embodiment.

FIG. 6 is a diagram illustrating an example of a display screen according to the second embodiment.

DESCRIPTION OF EMBODIMENTS

Embodiments of the present invention are described below with reference to drawings. Similar elements are denoted by similar reference numerals, and a duplicated description thereof is omitted.

A photoacoustic apparatus, which is a subject information acquisition apparatus according to a broad aspect of the present invention, acquires information in terms of a characteristic value (characteristic value information) for each of a plurality of positions in an inside of a subject by using a reception signal obtained by receiving a photoacoustic wave. In the present specification, the term "photoacoustic wave" is used to describe an acoustic wave that is generated when a light beam is absorbed, and it is also referred to as a photo-ultrasonic wave. It is also called an "acoustic wave", a "ultrasonic wave", a "sonic wave", or an "elastic wave", generated when light is absorbed.

The characteristic value information acquired according to the aspect of the invention, reflects the absorption factor of optical energy. Specific examples of characteristic values are a sound pressure (typically an initial sound pressure) of a generated acoustic wave, a light energy absorption density or absorption coefficient obtained from the initial sound pressure, a concentration of a substance included in a tissue, and the like. Information associated with a concentration of a substance is, for example, oxygen saturation, a total hemoglobin concentration, an oxyhemoglobin concentration, or a deoxyhemoglobin concentration, or the like. Alternatively, the concentration of a substance may be a glucose concentration, a collagen concentration, a melanin concentration, a volume faction of fat, water, or the like. 2-dimensional or 3-dimensional characteristic value distribution data may be generated based on characteristic values at a plurality of positions. The distribution data may be generated in the form of image data.

In embodiments described below, a subject information acquisition apparatus is mainly for use in diagnosis of malignant tumor or a blood vessel disease of a human or an animal or for use in follow-up with chemical treatment. Therefore, it is assumed that a subject is a part of a living body, and more specifically, a body part to be examined such as a breast or the like of a human or an animal.

First Embodiment

A configuration and a process associated with a subject information acquisition apparatus according to a first embodiment are described below.

Overall System Configuration

FIG. 1 is a schematic diagram illustrating a configuration of a photoacoustic apparatus according to the first embodiment. The photoacoustic apparatus according to the present embodiment includes, at least, a light source 100, a probe 106 including a conversion element 115 configured to receive a photoacoustic wave, and a signal processing unit 107 configured to acquire characteristic value information associated with an inside of a subject by using a reception signal output from the conversion element 115.

The light from the light source 100 travels via an optical waveguide 101. When the light reaches a light exit surface 102, the light emerges from the light exit surface 102. The light source 100 emits a plurality of light pulses with different wavelengths at different timings. The light 103 emitted from the light exit surface 102 strikes a subject 104, and reaches a light absorber 105 that is a target part in the subject. Typical examples of the light absorber 105 include a tumor, a blood vessel, a substance such as hemoglobin existing in a blood vessel, or the like in a living body. The light absorber 105 absorbs energy of light with different respective wavelengths, and generates respective photoacoustic waves. The generated photoacoustic waves travel in the subject and reach the conversion element 115.

The conversion element 115 (or each of conversion elements 115 when two or more conversion elements 115 are provided) outputs a time-series reception signal in response to receiving the photoacoustic wave. The output reception signal is input to the signal processing unit 107. The signal processing unit 107 receives as many reception signals as there area light pulses striking the subject.

The signal processing unit 107 generates characteristic value information associated with the inside of the subject based on the input reception signal. In a case where the photoacoustic apparatus is a photoacoustic microscope or the like, the probe may include only one conversion element 115. However, in a case where the photoacoustic apparatus is a biological information acquisition apparatus for examining a subject such as a breast or the like, the probe 106 may include a plurality of conversion elements 115.

Internal Configuration of Signal Processing Unit 107

Next, referring to FIGS. 2A and 2B, an internal configuration of the signal processing unit 107 according to the present embodiment is described below. FIG. 2A is a block diagram illustrating in detail functions of the signal processing unit 107 and a peripheral configuration according to the present embodiment. FIG. 2B is a block diagram illustrating a specific example of a configuration of the signal processing unit 107 according to the present embodiment. In the present embodiment, the signal processing unit 107 includes a signal acquisition unit 110, an information acquisition unit 111, a display controller 112, a control unit 114, and a specifying unit 113.

The signal acquisition unit 110 acquires a time-series analog reception signal output from each conversion element 115 for each channel, and performs signal processing including amplification of the reception signal, analog-to-digital conversion of the analog reception signal, storing of the digital reception signal converted from the analog signal, and the like.

The information acquisition unit 111 acquires characteristic value information for each position in the subject from the reception signal output from the signal acquisition unit 110. More specifically, the information acquisition unit 111 determines data (distribution data) of characteristic values at coordinates in a two- or three-dimensional space by reconstructing an image using the time-series reception signal for each channel. To reconstruct the image, some known methods may be used. For example, an universal back projection (UBP) method, a filtered back projection (FBP) method disclosed in PTL 2, or the like may be used. Alternatively, a delay and sum process may be used.

In the case of a photoacoustic microscope using focused light or in the case of a photoacoustic microscope with a probe using a focused acoustic wave, distribution data may be generated without performing the image reproduction process. More specifically, the probe 106 and the illumination light spot are moved relatively with respect to the subject using a scanning mechanism while the probe 106 receives photoacoustic waves at a plurality of scanning positions. The information acquisition unit 111 performs an envelope detection on the obtained time-varying reception signal, and then converts the time axis direction of the signals of the respective light pulses to a depth direction and plots the result in a spatial coordinate system. By performing the above process for each scanning position, it is possible to obtain distribution data.

Based on the characteristic information or the distribution data generated by the information acquisition unit 111, the display controller 112 generates image data to be displayed on the display unit 109. More specifically, image processing such as a luminance conversion, a distortion correction, extracting an area of interest, a log-arithmic compression, and/or the like is performed based on the distribution data. Furthermore, the display controller 112 also controls a displaying operation such as displaying of various display items together with distribution data, updating of a displayed image or the like in accordance with an instruction given by the specifying unit 113.

The specifying unit 113 sends information to the information acquisition unit 111 to specify an α value used by the information acquisition unit 111 in determining the characteristic value information based on the reception signal. The α value will be described in detail below with reference to formula (6).

The control unit 114 supplies control signals and/or data to blocks in the photoacoustic apparatus thereby to control the blocks. More specifically, the control unit 114 supplies a light emission command signal to the light source 100, a reception control signal to the conversion element 115 in the probe 106, and the like. The control unit 114 also controls the signal amplification performed by the signal acquisition unit 110, the analog-to-digital conversion timing, the storage of the reception signal, an operation of scanning the probe 106 performed by a scanning mechanism (not illustrated), and the like. The control unit 114 is connected to an input unit 108 operated by a user or an operator to input various instructions. Information input by the user to the input unit 108 is transferred to the control unit 114 from the input unit 108. The control unit 114 transmits and receives information to and from various units including the signal acquisition unit 110, the information acquisition unit 111, the display controller 112, and specifying unit 113. Furthermore, the control unit 114 may store a signal or data such as the reception signal, the generated distribution data, display image data, various measurement parameters, and/or the like.

Process Performed by Signal Processing Unit 107

In the present embodiment, the information acquisition unit 111 determines, as the characteristic value information, at least, information representing the sound pressure of the photoacoustic wave and information representing the oxygen saturation. The oxygen saturation is an example of the concentration information in the present specification, and more specifically, the oxygen saturation indicates the ratio of the amount of hemoglobin combined with oxygen to the total amount of hemoglobin in red blood cells.

To determine the oxygen saturation, it is necessary to determine the ratio of the absorption coefficient at a plurality of wavelengths (at least two wavelengths) as represented by formula (3). The initial sound pressure ($P_0$) in formula (3) represents a true value of a photoacoustic wave actually generated in the inside of a subject. On the other hand, there is a possibility that a calculated value of the initial sound pressure (hereinafter referred to as a sound pressure (PA)) obtained as a result of a calculation performed by the information acquisition unit 111 includes an influence by an attenuation of the photoacoustic wave that may occur in the subject. The calculated value may also include other influences such as system noise, artifact that may occur during the image reconstruction process, and/or the like. Therefore, PA and $P_0$ are not necessarily equal to each other. Thus, as shown below in formula (4), a parameter C is introduced to represent the overall effects of the attenuation of the acoustic wave, noise, and the like described above.

[Math. 4]

$$P_0^\lambda = C^\lambda \cdot PA^\lambda \tag{4}$$

where λ denotes the wavelength. Using formula (4), formula (3) may be rewritten as follows.

[Math. 5]

$$\frac{\mu_a^{\lambda_2}(r)}{\mu_a^{\lambda_1}(r)} = \frac{\Phi^{\lambda_1} \cdot P_0^{\lambda_2}}{\Phi^{\lambda_2} \cdot P_0^{\lambda_1}} \tag{5}$$

$$= \frac{\Phi^{\lambda_1} \cdot C^{\lambda_2} \cdot PA^{\lambda_2}}{\Phi^{\lambda_2} \cdot C^{\lambda_1} \cdot PA^{\lambda_1}}$$

Herein, as shown in formula (6), a new parameter α is further introduced to express all effects of wavelength-dependent parameters other than sound pressure (Φ and C in the case of formula (5)) in a single parameter.

[Math. 6]

$$\alpha = \frac{\Phi^{\lambda_1} \cdot C^{\lambda_2}}{\Phi^{\lambda_2} \cdot C^{\lambda_1}} \tag{6}$$

As may be seen, α is a value representable by a formula including the amount of light dependent on the wavelength.

Note that the Gruneisen coefficient Γ does not depend on the wavelength, and thus the Gruneisen coefficient is not included in formula (3) and formula (5). However, to take into account an effect of a change in temperature of the subject, the Gruneisen coefficient Γ may be incorporated in formula of α. Note that hereinafter, α having a value defined above will be referred to as an α value. Using the α value, formula (5) may be rewritten as follows.

[Math. 7]

$$\frac{\mu_a^{\lambda_2}(r)}{\mu_a^{\lambda_1}(r)} = \alpha \cdot \frac{PA^{\lambda_2}}{PA^{\lambda_1}} \quad (7)$$

That is, the α value is a coefficient of the sound pressure (PA) in a formula that determines the ratio of the absorption coefficients for different wavelengths. Thus, the oxygen saturation ($SO_2$) is given by formula (8) shown below.

[Math. 8]

$$SO_2(r) = \frac{\alpha \cdot \frac{PA^{\lambda_2}}{PA^{\lambda_1}} \cdot \varepsilon_{Hb}^{\lambda_1} - \varepsilon_{Hb}^{\lambda_2}}{(\varepsilon_{HbO}^{\lambda_2} - \varepsilon_{Hb}^{\lambda_2}) - \alpha \cdot \frac{PA^{\lambda_2}}{PA^{\lambda_1}} \cdot (\varepsilon_{HbO}^{\lambda_1} - \varepsilon_{Hb}^{\lambda_1})} \quad (8)$$

As described above, when the calculated value (PA) is determined by the calculation using the reception signal for each wavelength performed by the information acquisition unit 111, and the coefficient given by the α value is determined, then the oxygen saturation is obtained.

Next, a flow of a process performed by the signal processing unit 107 to determine an oxygen saturation distribution is described below. FIG. 3 is a flow chart illustrating a process of determining an oxygen saturation distribution according to the present embodiment. The flow illustrated in FIG. 3 starts from a state in which the signal acquisition unit 110 in the signal processing unit 107 has sequentially received signals from the probe for each wavelength of illumination light, and the signal acquisition unit 110 has performed the analog-to-digital conversion and the amplification on the received signals.

In S101, the information acquisition unit 111 acquires, using the input reception signals, distribution data of a sound pressure ($PA^{\lambda_1}$) at a first wavelength $\lambda_1$ and distribution data of a sound pressure ($PA^{\lambda_2}$) at a second wavelength $\lambda_2$.

In S102, the display controller 112 performs image processing based on the information of the sound pressure distribution of at least one of a plurality of wavelengths, and displays an image representing the sound pressure distribution on the display unit 109. Note that it is assumed herein by way of example that the image of the sound pressure distribution displayed represents a tomographic image at a particular depth in the inside of the subject. The depth of the tomographic image may be specified by a user or may be set in advance. Alternatively, in the present embodiment, the image of the sound pressure distribution displayed may be a 3-dimensional image in a particular region of the inside of the subject. In this case, the region displayed may be limited to a region in which a difference in amount-of-light ratio among wavelengths is negligibly small (that is, the amount-of-light ratio is substantially equal among wavelengths). The limitation in terms of the region displayed may be set by a user or may be set in advance.

In S103, the specifying unit 113 accepts information in terms of the α value input by a user and specifies this α value to be used by the information acquisition unit 111. At this stage, the user may be allowed to input an arbitrary value as the α value. As described later with reference to FIG. 4, to input the α value, the user may directly input a value or may specify a value by using a slide bar or the like.

In S104, the information acquisition unit 111 acquires oxygen saturation distribution data using distribution data of the sound pressure ($PA^{\lambda_1}$) at the wavelength $\lambda_1$ and distribution data of the sound pressure ($PA^{\lambda_2}$) at the wavelength $\lambda_2$. Herein it is assumed by way of example that the distribution data is generated within a range in which the distance (depth) from a light illuminated area on a subject surface and the distance (depth) from the probe can be regarded as being constant. Within this range, the attenuation of the light or the acoustic wave in the subject can be regarded as constant, and thus it is allowed to use the same α value for any position in the image in this range.

In S105, the display controller 112 generates image data based on the oxygen saturation distribution data generated by the information acquisition unit 111, and displays it on the display unit 109. Thus a user is allowed to check the displayed image of the oxygen saturation distribution as to whether the oxygen saturation distribution is likely to be correct. An example of a criterion for determining whether oxygen saturation is likely to be correct is to detect a position of an artery from the sound pressure distribution image displayed in S102 and determine whether the oxygen saturation at this position of the blood vessel is in a range around 95%. If the oxygen saturation at this position is in this range, it may be determined that the oxygen saturation seems to be true. In a case where there are accompanying blood vessels as in a case where an artery and a vein extend in parallel, a thinner one of the accompanying blood vessels may be assumed to be an artery, and under this assumption the determination may be made as to whether the oxygen saturation is true.

In S106, the control unit 114 receives judgment information input by a user. In a case where the judgment information indicates that oxygen saturation is highly likely to be correct, that is, in a case where the answer to S106 is YES, the processing flow is ended. However, in a case where the judgment information indicates that the oxygen saturation is not likely to be correct, that is, in a case where the answer to S106 is NO, the processing flow returns to S103.

In a case where the processing flow returns to S103, a changed α value input by a user is accepted, and then in S104 oxygen saturation distribution data is generated based on the changed α value. In S105, based on the new oxygen saturation distribution data, the image is changed from the oxygen saturation distribution image based on the previous α value to an oxygen saturation distribution image based on the changed α value. The above process is performed repeatedly until the judgment information input by the user indicates that the oxygen saturation is highly likely to be correct.

Note that in the second and following iterations of the process, the inputting of the α value in S103 may also serve to input the judgment information indicating NO (that is, indicating that the oxygen saturation is not likely to be correct) in S106. That is, in S106, it may be regarded that the judgment information is NO by receiving an α value input in the n-th iteration different from an α value input in an immediately previous iteration (that is, in the (n−1)th iteration). In this case, S103 in the immediately following iteration ((n+1)th iteration) may be skipped. On the other hand, in S106, in a case where an instruction to change the α value is not received, then it may be determined that the oxygen saturation is highly likely to be correct, and thus the processing flow is ended.

FIG. 4 is a diagram illustrating an example of a display screen displayed in S105. In FIG. 4, reference numeral 301 denotes a sound pressure distribution image at a wavelength ($\lambda_1$) generated in S102. Note that in S102, a sound pressure distribution image may be displayed for another wavelength ($\lambda_2$). Reference numeral 302 denotes an oxygen saturation distribution image acquired using the sound pressure distribution data for a plurality of wavelengths and the α value. Next to the image of the oxygen saturation distribution, an item (for example, a color bar) is displayed to provide guide information in terms of the correspondence between the luminance value and the oxygen saturation. When a user moves a cursor to an arbitrary position of interest (for example, a position of an artery) on the oxygen saturation distribution image, the oxygen saturation value at this position may be displayed. The displaying of the value of the oxygen saturation at the position of interest makes it easier for a user to visually determine whether the oxygen saturation is likely to be correct or not.

Reference numeral 303 denotes a slide bar for use by a user to input an α value. When a user slides this slide bar, the α value that is to be specified by the specifying unit 113 is changed. If the α value is changed, the oxygen saturation distribution image is updated. The display item for inputting the α value is not limited to the slide bar, but a box such as that denoted by reference numeral 304 may be employed such that a user is allowed to directly input a value in this box.

In the present embodiment, as described above, in the process of determining information in terms of the concentration of the oxygen saturation or the like, instead of a value of the amount of light actually measured by an amount-of-light sensor, an α value representable by a formula including an amount of light having each wavelength is used. This makes it possible to easily obtain an oxygen saturation distribution. Furthermore, in the present embodiment, it is allowed to change the α value to obtain an image of a more accurate oxygen saturation distribution. The information in terms of the concentration is not limited to the oxygen saturation, but the information may be of a total hemoglobin concentration, a concentration of oxyhemoglobin or deoxyhemoglobin, or the like. Alternatively, the information may be of a glucose concentration, a collagen concentration, or the like.

In the processing flow described above, it is assumed by way of example but not limitation that information in terms of the α value is input by a user, and, based on this input information, the specifying unit 113 gives the specified α value to the information acquisition unit 111. That is, the specifying unit 113 may give a value as the specified α value to the information acquisition unit 111 even when no α value is input by a user.

For example, a first value input as the α value does not necessarily need to be correct, and thus the specifying unit 113 may specify a particular value as the α value in S103 in a first iteration of the flow. Thereafter, the specifying unit 113 repeatedly performs the process of giving a value as the specified α value to the information acquisition unit 111 while gradually changing the α value until the judgment information input by a user indicates that the oxygen saturation distribution is likely to be correct. This also makes it possible to easily obtain an oxygen saturation distribution. Alternatively, a user may input subject information in terms of an age, a race, and/or the like of a person to be examined. When subject information is input, the specifying unit 113 may, in S103 in the first iteration, acquire an α value statistically derived from the input subject information and may employ this value as the specified value. Use of subject information makes it possible to more efficiently determine an oxygen saturation that is likely to be correct.

The process has been described above by way of example for a case where the oxygen saturation distribution is generated within a range in which the distance (depth) from a light illuminated area on a subject surface and the distance (depth) from the probe can be regarded as being constant, and thus the specifying unit 113 specifies the same α value for any position in the image. However, in a case where the distance from the light illuminated area and the distance from the probe vary depending on the position in the image, the specifying unit 113 may change the specified α value depending on the position in the subject. For example, in a case where the distance from the light illuminated area varies, the specifying unit 113 may specify the α value such that the α value exponentially increases as the distance increases. Also in a case where, in a particular region, the distance from the light illuminated area on the subject surface varies and/or the attenuation of the acoustic wave varies, which may occur, for example, in a case where the subject has a bent shape or has an unevenness, the specifying unit 113 may change the specified α value depending on the position in the region. On the other hand, in a case of a 3D image, the attenuation of light having each wavelength in the 3D region varies depending on the distance from the light illuminated area on the subject surface. In this case, the specifying unit 113 may change the specified α value depending on the distance from the light illuminated area.

Specific Example of Configuration of Signal Processing Unit 107

An example of an internal configuration of the signal processing unit 107 according to the present embodiment is described in detail below.

As for the signal acquisition unit 110, a circuit generally called a data acquisition system (DAS) may be used. More specifically, the signal acquisition unit 110 includes an amplifier that amplifies a reception signal, an analog-to-digital converter that convers the reception signal from analog form to digital form, and a memory such as FIFO, RAM, and/or the like for storing the reception signal.

As for the information acquisition unit 111, a processor such as a central processing unit (CPU), a graphics processing unit (GPU), or the like, or an operation circuit such as a field programmable gate array (FPGA), or the like may be used. Note that the information acquisition unit 111 may include only one processor or operation circuit or may include a plurality of processors and/or operation circuits.

The information acquisition unit 111 may further include a memory for storing the reception signal output from the signal acquisition unit 110. The memory typically includes a storage medium such as a ROM, a RAM, a hard disk, or the like. Note that the memory may include only one storage medium or may include a plurality of storage media.

The display controller 112, the specifying unit 113, and the control unit 114 may each be realized, as with the case of the information acquisition unit 111, using one of or a combination of a processor such as a CPU, a GPU, or the like or a circuit such as a FPGA chip or the like. Note that the display controller 112, the specifying unit 113, and the control unit 114 may include a memory for storing the reception signal, the generated distribution data, the display image data, various kinds of measurement parameters, and/or the like. The memory typically includes one or more storage media such as ROMs, RAMs, hard disks, or the like.

FIG. 2B illustrates a specific example of the signal processing unit 107 and examples of external units. In the example illustrated in FIG. 2B, the signal processing unit 107 includes a DAS 201, a memory 202, a CPU 203, and a GPU 204.

The DAS 201 provides one of functions of the signal acquisition unit 110 according to the present embodiment. A digital signal transferred from the DAS 201 is stored in the memory 202.

The CPU 203 provides part of functions of the control unit 114, the specifying unit 113, the display controller 112, and the information acquisition unit 111 according to the present embodiment. More specifically, the CPU 203 accepts various kinds of parameters and instructions associated with operations input by a user via the input unit 108, and the CPU 203 generates control information and controls the respective blocks via the system bus 200. The CPU 203 is also capable of performing signal processing such as an integrating process, a correction process, and the like on the digital signal stored in the memory 202. The CPU 203 may rewrite the digital signal subjected to the signal processing into the memory 202 such that the digital signal may be used by the GPU 204 in generating distribution data.

The GPU 204 provides part of functions of the information acquisition unit 111 and the display controller 112 according to the present embodiment. More specifically, generates distribution data using the digital signal that is stored in the memory 202 after being subjected to the signal processing performed by the CPU 203. Furthermore, the GPU 204 is capable of performing various kinds of image processing such as a luminance conversion, a distortion correction, extracting an area of interest, and/or the like on the generated distribution data. Note that part or all of the image processing or similar processing may be performed by the CPU 203.

Next, specific examples of configurations of units other than the signal processing unit 107 according to the present embodiment are described below.

Light Source 100

As for the light source 100, a pulsed light source may be used that is capable of generating pulsed light with a pulse width in a range from the order of nanoseconds to the order of microseconds. More specifically, for example, the pulse width may be in a range from 1 to 100 nanoseconds. The wavelength of the pulse may be in a range from 400 nm to 1600 nm. In particular, to perform imaging of a deep portion of a living body, the wavelength may be selected in a wavelength band called a "optical window in biological tissue" in which light is not absorbed much by a background tissue of the living body. More specifically, the wavelength may be in a range from 700 nm to 1100 nm. On the other hand, to get a high-resolution image of a blood vessel in the vicinity of a surface of a living body, the wavelength may be in a visible wavelength band. Note that a terahertz wave band, a microwave band, or a radio wave band may also be employed.

A specific example of a light source usable as the light source 100 is a laser. In the present embodiment, a plurality of wavelengths are used, and thus use of a laser capable of changing the oscillation wavelength may be advantageous. However, to illuminate the subject 104 with light with a plurality of wavelengths, a plurality of lasers that emit light with different wavelengths may be used and oscillation thereby may be switched. Alternatively, light may be emitted alternately by a plurality of lasers that emit light with different wavelengths. Also in a case where a plurality of lasers are used, a collective of them is referred to as a light source.

Examples of lasers usable as the light source 100 include a solid-state laser, a gas laser, a dye laser, a semiconductor laser, and so on. In particular, use of a pulsed laser such as a Nd:YAG laser, an alexandrite laser, or the like may be advantageous. Another choice is to employ a Ti:sa laser or an optical parametric oscillators (OPO) laser using a Nd:YAG laser light as excitation light. Instead of a laser, a light emitting diode or the like may be used.

Optical Waveguide 101 and Light Exit Surface 102

Light travels from the light source 100 to the subject 104 such that the light is transmitted via the optical waveguide 101 and the light exit surface 102. As for the optical waveguide 101 and the light exit surface 102, an optical element such as a lens, a mirror, an optical fiber, and/or the like may be used. Note that the subject may be directly illuminated by the light source 100 not through the optical element. In the case of a biological information acquisition apparatus designed to examine a breast or the like, the light exit surface 102 may be configured such that a light beam size is expanded by a lens or the like, and the expanded light strikes the breast or the like. On the other hand, in the case of a photoacoustic microscope, to increase the resolution, the light beam size may be reduced using a lens or the like such that a focused light beam strikes a target. The light exit surface 102 may be moved relative to the subject 104 to make it possible to achieve imaging over a wider area of the subject 104.

Probe 106

The probe 106 includes one or more conversion elements 115. Each conversion element 115 may be realized by an arbitrary conversion element capable of receiving an acoustic wave and converting received acoustic wave to an electric signal, such as a piezoelectric element using a piezoelectric phenomenon of lead zirconate titanate (PZT) or the like, a conversion element using optical resonance, a conversion element of a capacitance type such as CMUT, or the like. In a case where the probe 106 includes a plurality of conversion elements 115, it may be advantageous to arrange the conversion elements 115 in a flat or curved plane in a manner called a 1D array, a 1.5D array, a 1.75D array, a 2D array or the like.

In the case of a biological information acquisition apparatus designed to examine a breast or the like, to make it possible to perform imaging over a wide area, it may be advantageous that the probe 106 is configured to be mechanically movable relative to the subject. In a case where the probe 106 is of a handheld type, a user may move the probe 106 held in a user's hand. On the other hand, in the case of a photoacoustic microscope, it may be advantageous to employ, as the probe 106, a focusing-type probe configured to be mechanically movable along the surface of the subject 104. It may be also advantageous to move the probe 106 synchronously with the probe 106 of the illumination light 103.

The probe 106 may include an amplifier that amplifies an analog signal output from the conversion element 115.

Input Unit 108

As for the input unit 108, a mouse, a keyboard, a touch panel, a voice input unit, or the like may be used. The input unit 108 does not necessarily need to be included in the photoacoustic apparatus according to the present embodiment, but the input unit 108 may be separately disposed and may be connected to the photoacoustic apparatus.

Display Unit 109

As for the display unit 109, a display such as a liquid crystal display (LCD), a cathode ray tube (CRT) display, an organic electroluminescent display, or the like may be used. The display unit 109 does not necessarily need to be included in the photoacoustic apparatus according to the present embodiment, but the display unit 109 may be prepared separately from the photoacoustic apparatus and may be connected to the photoacoustic apparatus.

Second Embodiment

Next, a second embodiment is described. A photoacoustic apparatus according to the second embodiment is similar in configuration to the photoacoustic apparatus according to the first embodiment, and thus a duplicated description thereof is omitted. The signal processing unit 107 performs processing in a different manner from that according to the first embodiment, and thus the following description focuses on the difference from the first embodiment.

First, referring to FIG. 5, the processing performed by the signal processing unit 107 according to the second embodiment is described below. FIG. 5 is a flow chart illustrating the process performed by the signal processing unit 107 to determine an oxygen saturation distribution. The flow illustrated in FIG. 5 starts from a state in which the signal acquisition unit 110 in the signal processing unit 107 has sequentially received signals from the probe for each wavelength of illumination light, and the signal acquisition unit 110 has performed the analog-to-digital conversion and the amplification on the received signals.

In S501, the information acquisition unit 111 acquires distribution data of sound pressure ($PA^{\lambda_1}$) at the wavelength $\lambda_1$ and distribution data of sound pressure ($PA^{\lambda_2}$) at the wavelength $\lambda_2$ based on the input reception signal.

In S502, the display controller 112 performs image processing based on the information of the sound pressure distribution of at least one of a plurality of wavelengths, and displays an image representing the sound pressure distribution on the display unit 109. Note that it is assumed herein by way of example that the image of the sound pressure distribution displayed represents a tomographic image at a particular depth in the inside of the subject. The depth of the tomographic image may be specified by a user or may be set in advance. Alternatively, in the present embodiment, the image of the sound pressure distribution displayed may be a 3-dimensional image in a particular region of the inside of the subject. In this case, the region displayed may be limited to a region in which a change in amount-of-light ratio among wavelengths is negligibly small (that is, the amount-of-light ratio is substantially equal among wavelengths). The limitation in terms of the region displayed may be set by a user or may be set in advance.

In S503, the specifying unit 113 accepts information input by a user in terms of a position of interest via the input unit 108 and the control unit 114. In this case, the position of interest may be a position of a blood vessel of interest for which oxygen saturation is known, or may be a position of an artery for which oxygen saturation can be regarded as being in a small range around 95%. A user may specify a position of interest in the sound pressure distribution while watching the sound pressure distribution displayed.

Furthermore, in S503, the specifying unit 113 accepts an oxygen saturation value at the specified position of interest. The oxygen saturation value at the position of interest may be input by a user, or a value stored in advance in the control unit 114 may be employed. For example, in a case where a position of an artery is specified by a user as the position of interest, an oxygen saturation value (for example, 97%) of an artery stored in the control unit 114 may be input to the specifying unit 113.

In S504, the specifying unit 113 determines the $\alpha$ value at the position of interest according to formula (8) using input information in terms of the position of interest, sound pressure distribution data for two wavelengths, and the oxygen saturation at the position of interest. The specifying unit 113 specifies this $\alpha$ value to be used by the information acquisition unit 111.

In S505, the information acquisition unit 111 determines oxygen saturation at positions other than the position of interest using the specified $\alpha$ value, distribution data of the sound pressure ($PA^{\lambda_1}$) for the wavelength $\lambda_1$, and distribution data of the sound pressure ($PA^{\lambda_2}$) for the wavelength $\lambda_2$. As a result, in addition to the known oxygen saturation at the position of interest, the oxygen saturation at positions other than the position of interest is obtained, and thus the information acquisition unit 111 acquires oxygen saturation distribution data. In this processing flow, it is assumed by way of example that the distribution data is generated within a range in which the distance (depth) from a light illuminated area on a subject surface and the distance (depth) from the probe can be regarded as being constant. Within this range, the attenuation of the light or the acoustic wave in the subject can be regarded as constant, and thus it is allowed to use the same $\alpha$ value for any position in the image. Therefore, the specified $\alpha$ value given in S504 by the specifying unit 113 to the information acquisition unit 111 is applied not only to the position of interest but also to other positions in the image other than the position of interest.

In S506, the display controller 112 generates image data based on the oxygen saturation distribution data generated by the information acquisition unit 111, and displays it on the display unit 109.

An example of a display screen according to the present embodiment is described below with reference to FIG. 6. FIG. 6 is a diagram illustrating an example of a display screen according to the present embodiment. In FIG. 6, reference numeral 601 denotes a sound pressure distribution image at a wavelength ($\lambda_1$) generated in S501. Note that in S502, a sound pressure distribution image may be displayed for another wavelength ($\lambda_2$). Reference numeral 602 denotes an oxygen saturation distribution image generated in S504. Next to the image of the oxygen saturation distribution, an item (for example, a color bar) is displayed to provide guide information in terms of the correspondence between the luminance value and the oxygen saturation. Reference numeral 603 denotes a cursor for use by a user to input a position of interest in S503. A user is allowed to specify the position of interest by moving the cursor using the input unit 108. Information indicating the position of interest is input to the specifying unit 113. If the position of interest or the oxygen saturation at the position of interest is changed, an image of an oxygen saturation distribution denoted by reference numeral 602 is updated.

Reference numeral 604 denotes a box for use in S503 by a user to directly input a value of oxygen saturation at the position of interest. Instead of a display item such as a box, a slide bar denoted by reference numeral 605 may be used to input an oxygen saturation value.

Also in the present embodiment, as described above, when information in terms of the concentration such as oxygen saturation or the like is determined, instead of a value of the amount of light actually measured by an amount-of-light sensor, an α value representable by a formula including an amount of light having each wavelength is used. This makes it possible to easily obtain an oxygen saturation distribution. Furthermore, in the present embodiment, a position of interest at which it is possible to estimate oxygen saturation is specified. This makes it possible to easily obtain an oxygen saturation distribution image with a high likelihood of being true. The information in terms of the concentration is not limited to the oxygen saturation, but the information may be of a total hemoglobin concentration, a concentration of oxyhemoglobin or deoxyhemoglobin, or the like. Alternatively, the information may be of a glucose concentration, a collagen concentration, or the like.

In the processing flow described above, a user specifies a position of interest, and the specified position of interest is input to the specifying unit 113. However, in the present embodiment, the manner of specifying the position of interest is not limited to that described above. For example, when no information as to the position of interest is given by a user, the control unit 114 may give information specifying the position of interest to the information acquisition unit 111. More specifically, in a case where a shape of a blood vessel of interest such as an artery or the like is known, the control unit 114 may be capable of automatically identifying a position of the blood vessel of interest using a pattern matching method or the like. For example, by automatically extracting an accompanying blood vessel, it is possible to identify the position of the blood vessel of interest.

In the pattern matching, the control unit 114 stores template data representing shapes of particular blood vessels having a possibility of being specified as a blood vessel of interest. The template data may be generated by a simulation or an actual measurement. When data of a particular part of an image of a sound pressure distribution is similar to template data, there is a high probability that this particular part of the image is of the blood vessel of interest. Thus, the control unit 114 extracts a part of the sound pressure distribution and calculates the similarity of the extracted part with respect to the template data. The control unit 114 performs the similarity calculation repeatedly while changing the part extracted from the sound pressure distribution. The similarity may be calculated using zero-mean normalized cross-correlation (ZNCC). Alternatively, to calculate the similarity, a parameter such as a sum of squared difference (SSD), a sum of absolute difference (SAD), or the like indicating the similarity may be used.

In the iterative calculation of the similarity, the control unit 114 detects a position at which the similarity is higher than a threshold value thereby extracting an image similar to the template data (that is, an image of a blood vessel of interest).

The process has been described above by way of example for a case where the oxygen saturation distribution is generated within a range in which the distance (depth) from a light illuminated area on a subject surface and the distance (depth) from the probe can be regarded as being constant. Therefore, in S504, under the assumption that the same α value is to be applied to the position of interest and the other positions, the specifying unit 113 specifies the α value for the position of interest. However, in a case where the distance from the light illuminated area and the distance from the probe vary depending on the position in the image, the specifying unit 113 may specify different a values for different positions. For example, in a case where the distance from the light illuminated area varies, the specifying unit 113 may specify the α value such that a value exponentially increases as the distance increases.

Also in a case where the distance from the light illuminated area on the subject surface varies and/or the attenuation of the acoustic wave varies, the specifying unit 113 may change the specified α value depending on the position in the region. On the other hand, in a case of a 3D image, the attenuation of light having each wavelength in the 3D region varies depending on the distance from the light illuminated area on the subject surface. In this case, the specifying unit 113 may change the specified α value depending on the distance from the light illuminated area.

To give the specified α value so as to vary depending on the position, a specific example of a process is as follows. When a position of interest such as a position of an artery or the like is specified in S503, the whole artery of interest is extracted from the image based on the connection from the specified position.

Thereafter, in S504, the α value is calculated for each position of the artery from the sound pressure distribution data of two wavelengths over various positions of the artery and an oxygen saturation value (for example, 97%) of the artery. The specifying unit 113 gives, as specified values, the α values determined for respective positions of the artery to the information acquisition unit 111. Next, in S505, using the specified α values at various position, distribution data of the sound pressure ($PA^{\lambda_1}$) at the wavelength $\lambda_1$, and distribution data of the sound pressure ($PA^{\lambda_2}$) at the wavelength $\lambda_2$, the information acquisition unit 111 determines the oxygen saturation at various positions in the vicinity of the position of interest or at various positions in a region in which the distance (depth) from the light illuminated area on the subject surface and the distance (depth) from the probe can be regarded as constant. As a result of performing the process in the above-described manner, the oxygen saturation at each position other than the position of interest, that is, at each position close to the artery of interest is obtained as well as the known oxygen saturation at the position of interest, and thus the information acquisition unit 111 is capable of acquiring the oxygen saturation distribution data over the artery and over a region close to the artery.

The method described above may also be applied to a 2D image. Although a position of an artery is specified as a position of interest in the example described above, another position may be specified as long as oxygen saturation at that position is known.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-089307, filed Apr. 23, 2014, which is hereby incorporated by reference herein in its entirety.

The invention claimed is:

1. A photoacoustic apparatus comprising:
a light source configured to generate a plurality of light beams having wavelengths λ1 and λ2 different from each other;
a conversion element configured to receive a photoacoustic wave that is generated in a subject in response to being illuminated with the light beams having wavelengths λ1 and λ2 different from each other and output a signal for each wavelength;
an information acquisition unit configured to acquire information in terms of a concentration of a substance existing in the subject by using the signal output for each wavelength; and
a specifying unit configured to specify a coefficient and instruct the information acquisition unit to use the specified coefficient in acquiring the information in terms of the concentration,
wherein the specifying unit specifies the coefficient as a single parameter α in a formula (6)

$$\alpha = \frac{\Phi^{\lambda_1} \cdot C^{\lambda_2}}{\Phi^{\lambda_2} \cdot C^{\lambda_1}} \quad (6)$$

where each one of $\Phi^{\lambda_1}$ and $\Phi^{\lambda_2}$ respectively denotes a light fluence in the different wavelengths λ1 and λ2, and each one of $C^{\lambda_1}$ and $C^{\lambda_2}$ respectively denotes an attenuation of the photoacoustic wave in association with the different wavelengths λ1 and λ2, and
wherein the information acquisition unit acquires information in terms of the concentration by using the coefficient specified by the specifying unit and the signal for each wavelength.

2. The photoacoustic apparatus according to claim 1, wherein the plurality of light beams generated by the light source includes a light having a first wavelength and a light having a second wavelength different from the first wavelength,
wherein the specifying unit specifies, as the coefficient, a value representable by the formula (6) including a ratio of an amount of light having the first wavelength and an amount of light having the second wavelength, and
wherein the information acquisition unit acquires the information in terms of the concentration by further using the value specified by the specifying unit, a signal associated with the light having the first wavelength, and a signal associated with the light having the second wavelength.

3. The photoacoustic apparatus according to claim 1, wherein the plurality of light beams generated by the light source includes a light having a first wavelength and a light having a second wavelength different from the first wavelength,
wherein the information acquisition unit determines a sound pressure of a photoacoustic wave generated in the subject by the light having the first wavelength and a sound pressure of a photoacoustic wave generated in the subject by the light having the second wavelength, and
wherein the information acquisition unit acquires the information in terms of the concentration by using the coefficient given by the specifying unit, and excluding parameters indicating a sound pressure associated with the light having the first wavelength, and a sound pressure associated with the light having the second wavelength.

4. The photoacoustic apparatus according to claim 1, wherein the formula (6) includes a value associated with an attenuation of the photoacoustic wave in the subject.

5. The photoacoustic apparatus according to claim 1, wherein in response to receiving from a user an instruction to change the coefficient, the specifying unit changes the coefficient.

6. The photoacoustic apparatus according to claim 5, wherein the information acquisition unit acquires the information in terms of the concentration based on the coefficient having a not-yet-changed value and the concentration based on the coefficient having a changed value.

7. The photoacoustic apparatus according to claim 6, further comprising a display controller configured to control displaying of a display unit,
wherein the display controller controls the display unit to display the information in terms of the concentration based on the coefficient having the not-yet-changed value and the information in terms of the concentration based on the coefficient having the changed value.

8. The photoacoustic apparatus according to claim 7, wherein the display controller controls the display unit to display an item for accepting an input in terms of the coefficient given by a user.

9. The photoacoustic apparatus according to claim 7, wherein
based on a signal associated with the light having a first wavelength among the plurality of light beams having different wavelengths, the information acquisition unit determines information representing a sound pressure of a photoacoustic wave generated by the light having a first wavelength at each of a plurality of positions in the subject thereby acquiring sound pressure distribution data, and
the display controller controls the display unit to display the sound pressure distribution data.

10. The photoacoustic apparatus according to claim 9, wherein the specifying unit accepts specification from a user in terms of a position of interest in the sound pressure distribution.

11. The photoacoustic apparatus according to claim 10, wherein the specifying unit acquires a coefficient at a position other than the position of interest based on information in terms of a concentration of the substance at the position of interest, and the information acquisition unit acquires information in terms of a concentration of the substance at the position other than the position of interest based on the coefficient at the position other than the position of interest.

12. The photoacoustic apparatus according to claim 9, wherein the specifying unit extracts a position of interest based on the sound pressure distribution data.

13. The photoacoustic apparatus according to claim 1, wherein the information acquisition unit is further configured to determine information representing oxygen saturation as the information in terms of the concentration.

14. The photoacoustic apparatus according to claim 13, wherein the information acquisition unit determines the information representing oxygen saturation at each of a plurality of positions in the subject thereby acquiring oxygen saturation distribution data.

15. The photoacoustic apparatus according to claim 1, wherein the specifying unit changes the value of the specified coefficient depending on a position in the subject.

16. The photoacoustic apparatus according to claim 1, wherein the information acquisition unit acquires, by using the coefficient, information in terms of the concentration at each of a plurality of positions within a range in which a distance from a light illuminated area on a subject surface can be regarded as being constant.

17. A method of acquiring subject information, comprising:

acquiring information in terms of a concentration of a substance existing in a subject by using a signal output from a conversion element that receives a photoacoustic wave respectively generated in the subject in response to being illuminated with a plurality of light beams having different wavelengths from each other; and specifying a coefficient for use in acquiring the information in terms of the concentration, wherein, in the specifying of the coefficient, a single parameter α is specified in a formula (6)

$$\alpha = \frac{\Phi^{\lambda_1} \cdot C^{\lambda_2}}{\Phi^{\lambda_2} \cdot C^{\lambda_1}} \tag{6}$$

where each one of $\Phi^{\lambda_1}$ and $\Phi^{\lambda_2}$ respectively denotes a light fluence in the different wavelengths λ1 and λ2, and each one of $C^{\lambda_1}$ and $C^{\lambda_2}$ respectively denotes an attenuation of the photoacoustic wave in association with the different wavelengths λ1 and λ2, and wherein, in the acquiring of the information, the information in terms of the concentration is acquired using the specified coefficient and the signal for each wavelength.

18. A non-transitory computer readable medium storing a program that causes a computer to execute the control method according to claim 17.

* * * * *